United States Patent [19]
Moody et al.

[11] 4,080,832
[45] Mar. 28, 1978

[54] AIR SAMPLING MONITOR

[75] Inventors: Norman Frank Moody, Toronto; Ivan Paul Clark, Mississauga, both of Canada

[73] Assignee: The Governing Council of the University of Toronto, Toronto, Canada

[21] Appl. No.: 764,592

[22] Filed: Feb. 1, 1977

[51] Int. Cl.² ............................................. G01N 1/24
[52] U.S. Cl. ............................................. 73/421.5 R
[58] Field of Search ............... 73/421.5 R, 422 TC, 73/28; 417/412, 413, 415

[56] References Cited
U.S. PATENT DOCUMENTS

| | | | |
|---|---|---|---|
| 2,465,554 | 3/1949 | Roy | 417/415 |
| 3,387,748 | 6/1968 | Brenchley | 73/422 TC |
| 3,802,250 | 4/1974 | Garnier | 73/28 |

*Primary Examiner*—S. Clement Swisher
*Attorney, Agent, or Firm*—Hirons and Rogers

[57] ABSTRACT

A small, compact, portable air sampler, for wearing by an industrial worker to monitor the nature of the air breathed by the worker during work shifts, comprises an air filter and a pumping means adapted to draw a known volume of air through the filter on each stroke of the pumping means. The pumping means is controlled to draw air through the filter intermittently, at pre-selected intervals. An electronic clock determines the intervals, and a memory is provided to record the number of pumping strokes made during the period in which the instrument is worn by the worker, so that the total volume of air drawn through the sampler is known. The electronic controls and a power pack, along with the filter, pumping means and driving means, are all included in a housing, to provide a self-contained, miniaturized unit. A pocket clip is provided, for attachment to a wearer's clothing, with an electric switch which closes when the sampler is worn. Only when the switch is closed will the air sampler draw in air.

8 Claims, 5 Drawing Figures

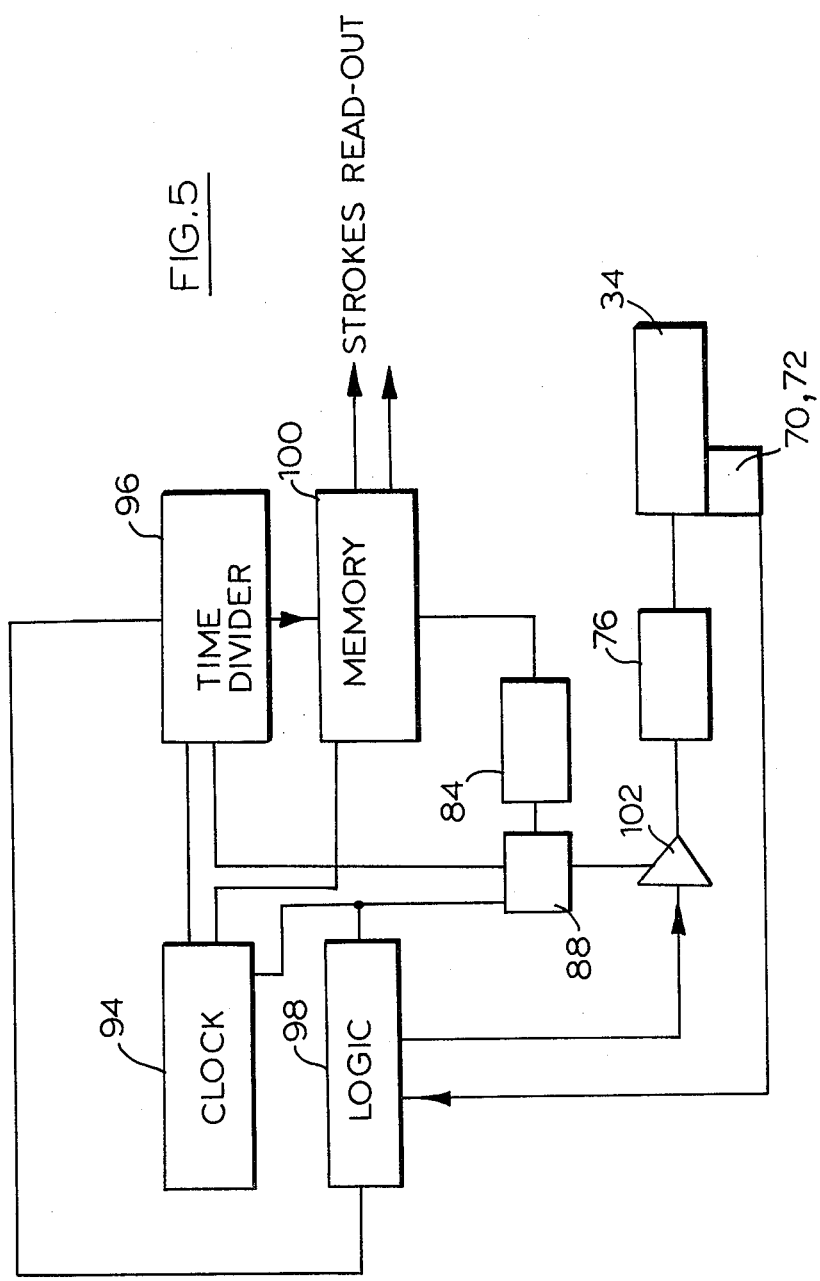

AIR SAMPLING MONITOR

FIELD OF THE INVENTION

This invention relates to air sampling devices, of the type which can be worn or carried by an individual for monitoring the air breathed by the individual.

BACKGROUND OF THE INVENTION

There is a growing awareness of the hazards to which individuals such as miners, factory workers and others are exposed during the extended periods of time which they spend in atmospheres containing airborne particulate matter (e.g. asbestos, silicates, ceramics) or a variety of gases. This arises particularly in connection with industrial workers. Employers may even be subject to heavy legal liability years after employee exposure to harmful substances. There is therefore a need to monitor the quality of the air which such an individual is breathing over a period of time, so as to be able to determine its quality, and its content of potentially harmful constituents.

BRIEF DESCRIPTION OF THE PRIOR ART

The monitoring practice commonly adopted at present is to equip certain selected workers with an air sampler at the start of a work shift, and collect it from the worker at the end of an 8 hour shift. However, previously proposed apparatus for this purpose has tended to be bulky, heavy and expensive. Such instruments are inconvenient for the wearer. They need recharging at the end of 8 hours so that their use is severely restricted. Further, sampling of air over an 8 hour period is likely to be unrepresentative; a lung burden experienced by a worker over a longer period of time such as 28 days is physiologically much more significant.

BRIEF SUMMARY OF THE INVENTION

It is an object of the present invention to provide a novel air sampling device.

It is a further object to provide an air sampling device which is light and compact, and can be conveniently worn by an individual.

It is a further object to provide an air sampling device which requires no operation of controls or adjustment by the wearer, and which can run without attention for extended periods of time.

According to the present invention, there is provided a portable air sampler comprising an air filter having an inlet side in communication with an atmosphere to be sampled, an air pumping means adapted to draw a predetermined volume of air through the filter from said atmosphere to be sampled, driving means actuating the air pumping means, a timer controlling the driving means and adapted to cause the driving means to actuate the air pumping means at pre-selected intervals to draw the predetermined volume of air through the air filter, and a counting means associated with the driving means and adapted to count and record the number of actuations of the air pumping means during a given time period.

By means of the present invention, samples of air over extended period of time, for example 28 days, can be taken, and the particulate and other matter collected by the filter over such a period of time can be removed and analyzed so as to give a representative evaluation of the quality of air breathed by the individual who has worn the sampler over such extended periods of time. The device keeps a record of the total volume of air which has been drawn through the filter and hence sampled, since the device uses an air pumping means which draws a predetermined volume of air through the filter on each stroke, and a record is kept by the counting means of the number of strokes of the air pumping means during the given interval. Thus the device of the invention allows a proper assessment of the lung burden to which the individual wearing the device has been subjected during the extended period of time that it has been used.

DESCRIPTION OF THE PREFERRED EMBODIMENTS

Preferably, the air sampler according to the present invention is small, compact, readily portable unit comprising a housing enclosing all or most of the operating parts. The air filter may be mounted in an aperture in a wall of the housing with the inlet side of the air filter presented towards the exterior of the housing or in a tube connected to and adapted to feed air to the housing. The air pumping means, and other associated parts, are mounted within the housing so as to form a compact, self-contained unit. The air pumping means is mounted in communication with the outlet side of the air filter. This same housing means suitably also encloses the driving means, the timer and the counting means, and also a power pack such as a battery, for providing electrical power to the various components.

In such an arrangement, the small, compact, self-contained device according to the invention requires no external control or adjustment by the wearer. In fact, the sampler according to the invention can be miniaturized to a size to fit into a shirt pocket, so as to be easily worn in a pocket, or on a belt, with the inlet filter protruding therefrom.

According to another preferred feature of the invention, the air pumping means comprises an expandable and contractable bellows cylinder, having a substantially air impermeable side wall. The difference between the internal volume of the bellows cylinder in the expanded position and the internal volume thereof in the contracted position corresponds to the pre-determined volume of air which is drawn through the filter on each stroke, the driving means being adapted to drive the bellows cylinder from its expanded volume condition to its contracted volume condition and back again.

Preferably also, the bellows cylinder includes outlet valves, through which air is expelled when the bellows cylinder is moved to its contracted condition, but which close when the bellows cylinder is moved back to its expanded condition. Inlet valves are also preferably provided, which close when the bellows cylinder moves from its expanded to its contracted position, but open when it moves from its contracted to its expanded condition, the communication between the filter and the bellows cylinder being via the inlet valves. In such an arrangement, air is expelled from the inside of the bellows cylinder through the outlet valves in such a manner that it does not disturb the filter and the materials collected thereon. On the movement to the expanded condition, the sample of air is drawn into the interior of the bellows cylinder, through the filter and the inlet valves. This air remains trapped in the interior of the bellows cylinder, until the next stroke, when it is expelled.

It will be appreciated that the air receiving means is actuated at intervals automatically by the timing means, rather than being in a continuous sampling condition. The intervals between various acutations of the air receiving means can be preadjusted, for example to operate once per minute, to take an air sample.

According to a further preferred embodiment of the invention, there is provided a pocket switch for the air sampling monitor in the form of a clip, which is switched to the on position when the individual attaches the air sampler to his clothing, but reverts to the off position when the sampler is removed from the clothing. By means of such an arrangment, an individual can wear the air sampling monitor and take samples therewith during a work shift, and leave the mechanics thereof inactive whilst in other environments, with the memory retaining a record of the number of previous strokes.

BRIEF REFERENCE TO THE DRAWINGS

FIG. 5 is a block diagram of the control and the driving means of the air sampling device of FIG. 1.

In the drawings, like reference numerals indicate like parts.

DETAILED DESCRIPTION OF THE PREFERRED EMBODIMENTS

Figure 1:
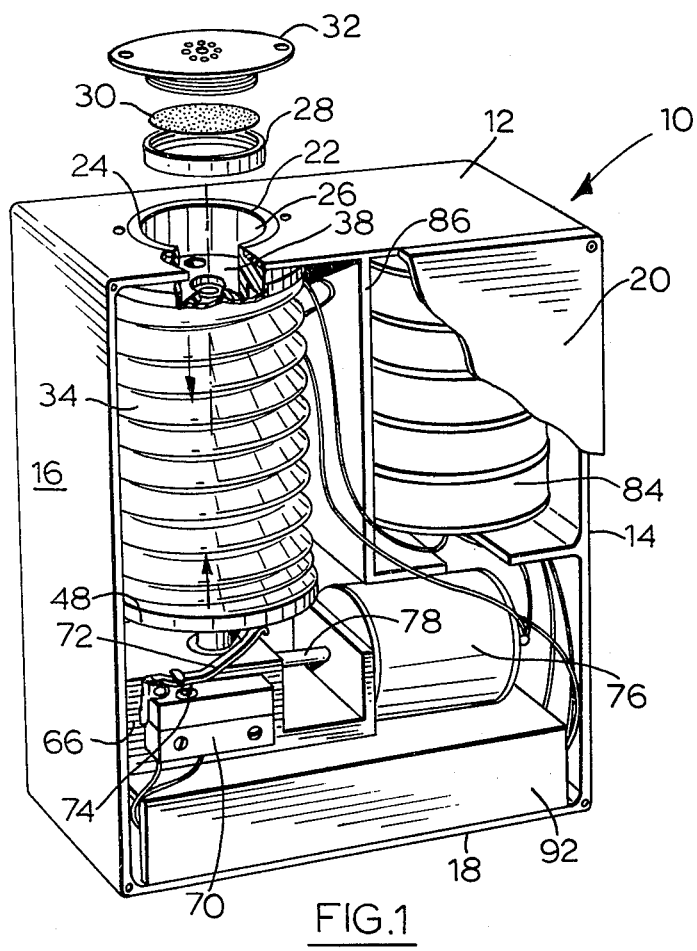
FIG. 1 is a perspective view of the front of an air sampling monitor according to a specific preferred embodiment of the invention, with the front cover of the housing and other parts cut away to show the arrangement of component parts.

With reference to FIG. 1, the portable air sampler 10 comprises a box-like housing having a top wall 12, side walls 14, 16, a bottom wall 18 and a removable front wall 20. A circular aperture 22 is located in the top wall 12, the aperture 22 being lined with a cup-shaped member 24 fixed therein, and forming a cavity 26 in the top wall 12. The bottom part of cup-shaped member 24 projects into the interior of the body. A retaining ring 28 is provided which has internal formations to hold therein a filter disc 30, sich as a millipore filter. The retaining ring 28 holding filter disc 30 is received in cavity 26 and is screwed into the underside of cover plate 32 in an air tight manner to prevent air entering around the sides of filter disc 30. An apertured cover plate 32 is also provided, which fits over and protrudes into the cavity 26. The cover plate 32 can be releasably fastened to the top wall 12 by means of screws.

Figure 2:
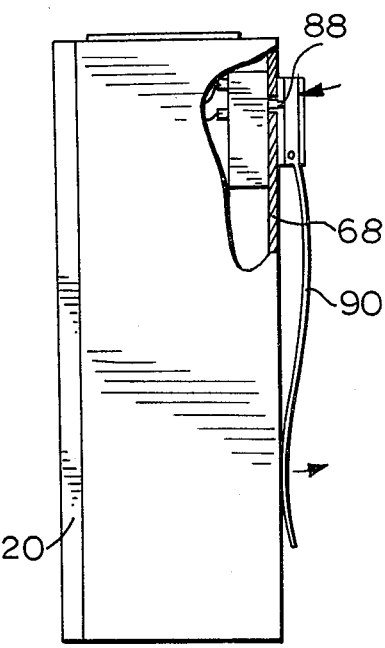
FIG. 2 is a side view of the device of FIG. 1.

Inside the housing and immediately below the cavity 26 in the top wall 12 is provided an expandable and collapsible air receiving means in the form of a bellows cylinder 34 having a concertina-like collapsible side wall of circular cross-section, the side wall thereof being of flexible, substantially air impermeable material such as rubber. At its upper end the bellows 34 is mounted on the periphery of an annular mounting flange 36 of the cup-shaped member 24, inside the top wall 12, in a substantially air-tight manner (FIG. 2). The integral bottom circular wall 38 of cup 24 thus effectively constitutes a substantial part of the upper end wall of bellows 34. Wall 38 is provided with ports 40, 42 therein with respective flaps 44, 46 opening into the interior of the bellows 34, these ports and flaps constituting inlet valves into the bellows cylinder 34 and opening when pressure inside the bellows cylinder 34 is reduced.

The bellows 34 is provided with a centrally apertured circular bottom end wall 48, in sealing engagement with the bottom of the flexible wall of the bellows. The end wall 48 has ports 50, 52 with respective flaps 54, 56 opening outwardly from the bellows 34, these ports and flaps constituting outlet valves for the bellows 34, openable in response to increase of pressure therein.

The bellows 34 is further provided with a central rotatable shaft 58 with helical grooves therein extending in both senses, so that the central shaft constitutes a continuous reversible feed screw. The upper end of shaft 58 is journalled for rotation in a ball bearing 60 in the bottom wall 38 of cup 24, constituting the upper end wall of the bellows cylinder 34. The shaft 58 at its lower end passes through a ball bearing ring 62, in the bottom end wall 48. A follower 64 protrudes inwardly from the periphery of bearing 62 in the bottom end wall, to engage in the helical grooves in the shaft 58, so that end wall 48 will raise and lower when shaft 58 is rotated.

A mounting bracket 66 is firmly secured to the interior of the side wall 16 and rear wall 68 of the sampler 10, to the front of which is secured a microswitch 70 which acts as a limit switch. The arm contact actuator 72 of the limit switch is of spring metal and is pushed downwardly by the bottom end wall 48 of the bellows 34 in the expanded position, to engage and close the limit switch 70. The end flange of the mounting block 66 remote from the limit switch 70 carries an electric motor 76, the drive shaft 78 of which extends horizontally through the bracket of mounting block 66. The end of drive shaft 78 carries a worm gear 80 meshing with a pinion 82 on the bottom of shaft 58 of the bellows 34, so as to drive the bellows 34 to expand and contract it.

A power pack, in the form of a 6¼ volt rechargeable battery 84 is provided in the housing, in a compartment alongside the bellows 34, defined by a dividing wall 86. A miniature pocket switch 88 is provided in the rear wall 68 of the housing, associated with a resilient clip 90, adapted to retain the sampler 10 on a person's belt, clothing or the like. This is best seen in FIG. 2. When the clip 90 is drawn away from engagement with the rear wall 68, e.g. when the sampler is hooked to a person's clothing by means of clip 90, pocket switch 88 is closed to form electrical contact. The pocket switch 88 is electrically associated with the power pack 84, as described below.

The mounting block 66 of the sampler carries thereon an electrical control module 92 to control automatically the operation and functioning of the unit. This control unit includes an electronic clock, a time dividing circuit, a motor control system, a counter and a memory, all of which are comprised of known, standard miniaturized electronic components, well known to those skilled in the art, so that details of their circuitry do not need to be described. FIG. 5 of the accompanying drawings illustrates the various electronic units of the control module 92 in a diagrammatic block form, from which their interrelationship and functioning in the device will be readily apparent.

Thus with reference to FIG. 5, the electrical control module 92 comprises an electronic clock 94, a time divider 96, and logic 98, each of which is electrically connected to the power pack 84 via the pocket switch 88, so that operating power is supplied to them only when pocket switch 88 is closed. A memory 100 is provided, continuously powered by power pack 84, and fed signals from the time divider 96 and the clock 94, so that the memory provides a recording and read-out of the number of strokes of expansion and collapse of the bellows 34, caused by actuation of motor 76. The logic 98 controls the operation of motor 76 via an amplifier 102, the logic 98 itself being responsive to opening and closing of limit switch 70. The logic 98 can be set to actuate motor 76 at predetermined intervals.

Figure 3:
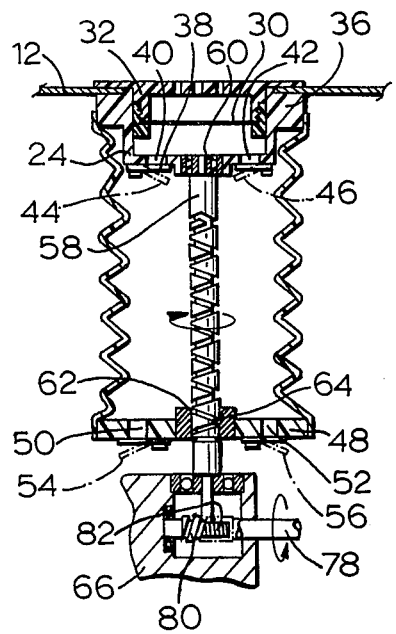
FIG. 3 is cross-sectional view of the air receiving means and associated parts, in an expanded position.
Figure 4:
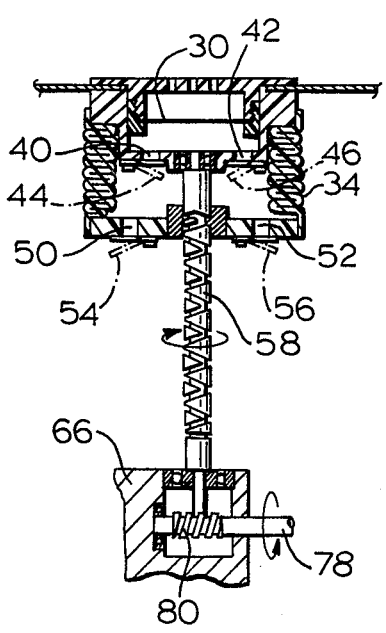
FIG. 4 is a view similar to FIG. 3 with the air receiving means in a collapsed position.

In operation, the assembled unit 10 is worn by the person by attaching it to a suitable portion of clothing such as a pocket, belt or the like, by means of clip 90, thereby closing pocket switch 88, with the cover plate 32 exposed to the atmosphere. The closing switch 88 starts the electronic clock 94, and time in operation is thus recorded in memory 100. The logic 98 is set to actuate the motor 76 at predetermined intervals, such as once per minute, overriding limit switch 70 to cause the bellows 34 to move from the expanded position shown in FIG. 3 to the collapsed position shown in FIG. 4, and back to the expanded position shown in FIG. 3. When the expanded position is resumed, limit switch 70 operates to stop further actuation of motor 76 until the next stroke. As bellows 34 is moved to the collapsed position of FIG. 4, flaps 54, 56 open to open ports 50, 52 to expel air from inside bellows 34. The upper flaps 44, 46 close during this operation to seal ports 40, 42 and prevent air being drawn through the filter. On the down stroke to expand the bellows 34, the action of the inlet and outlet valves is reversed, so that air from the environment is drawn in through the filter 30, into the interior of the bellows 34, through inlet ports 40, 42. This operation is repeated at the set intervals as long as the pocket switch 88 remains closed.

After a set period of time, the sampler 10 is recovered from the wearer, and the filter 30 is removed and analysed to determine the nature and quantity of material trapped thereby. From the memory 100, there is read out the number of strokes the bellows has made. From this figure, and a knowledge of the volume of the air sampled per stroke by the bellows 34, a determination of the amounts and nature of foreign air-suspended particulate matter breathed by the wearer during a given period of exposure to a working environment, can readily be determined.

The sampler according to the invention is readily adapted to measure quantities of a variety of different air pollutants, by choice of a suitable filter element, physical or chemical in nature, through which the air from the environment is drawn. Not only air borne particulate matter, but also pollutant gases, may be monitored on this manner and using a device according to the invention.

Moreover, the device of the present invention can be manufactured in small, compact size of very light weight, so that it offers a minimum of inconvenience to the wearer. Further, once set, it operates automatically for the predetermined, quite extensive period of time, without requiring attention, regulation, adjustment or control by the wearer himself.

It will be appreciated that the specific embodiment of the invention described in detail herein is illustrative only, and is not to be construed as limiting. The scope of the present invention is limited only by the appended claims.

We claim:

1. A portable air sampler comprising:
   a housing,
   an air filter mounted in an aperture in the housing and having an inlet side in communication with atmosphere to be sampled;
   an air pumping means within the housing and adapted to draw a predetermined volume of air through said filter from atmosphere to be sampled;
   a self-contained power pack within said housing;
   driving means within the housing, actuating said air pumping means, and electrically powered by said power pack;
   a timer within the housing, controlling the driving means and adapted to cause the driving means to actuate the air pumping means intermittently at preselected intervals to draw said predetermined volume of air through said air filter, the timer being electrically powered by said power pack;
   counting means within the housing, associated with said driving means and adapted to count and record the number of actuations of the air pumping means during a given time period, said counting means being electrically powered by said power pack.

2. The air sampler of claim 1 wherein the air pumping means comprises a vessel arrangeable in an expanded volume condition and a contracted volume condition, the difference between the internal volume of the vessel in the expanded volume condition and the internal volume thereof in the contracted volume condition corresponding to said predetermined volume of air to be drawn through said filter, the driving means being arranged to drive the air pumping means between its expanded volume condition and its contracted volume condition.

3. The air sampler of claim 2 wherein the air pumping means is an expandable and contractable bellows cylinder having flexible, foldable substantially air impermeable side walls, said bellows cylinder also including at least one outlet valve which opens to permit escape of air therethrough when the bellows cylinder is driven to its contracted condition and closes when the bellows cylinder is driven to its expanded condition, and including at least one inlet valve by means of which the bellows cylinder communicates with the outlet side of said air filter, the inlet valve being closed when the bellows cylinder is driven to its contracted condition and open when the cylinder is driven to its expanded condition.

4. The air sampler of claim 3 wherein said bellows cylinder has a central rotatable shaft extending through the cylinder from the end thereof which is in communication with the outlet side of the air filter, and having helical grooves therein, to constitute a continuous reversible feed screw, and a follower in the bottom end wall engaging said helical grooves, the driving means being adapted to rotate the shaft and cause the bottom end wall thereof to move along the rotating shaft to move the bellows cylinder between its expanded and its contracted conditions.

5. The air sampler of claim 1 further including an external clothing attachment means and an associated pocket switch electrically connected to the power pack, said pocket switch adapted to be electrically closed when the clothing attachment means is operated to attach the sampler to a wearer's clothing, and electrically open to cut off power from the power pack when the clothing attachment means is inoperative.

6. The air sampler of claim 5 further including an electrical limit switch electrically connected to the driving means and located in a fixed position with respect to the bellows cylinder, said limit switch being engaged by the bellows cylinder on reaching the expanded position thereof to interrupt power supply to the driving means.

7. The air sampler of claim 6 wherein the air filter is removable from the housing.

8. A portable air sampler comprising:
a housing;
an air filter mounted in an aperture in the housing and having an inlet side in communication with atmosphere to be sampled;
an air pumping means within the housing and adapted to draw a predetermined volume of air through said filter from atmosphere to be sampled;
driving means within the housing, actuating said air pumping means;
a timer within the housing, controlling the driving means and adapted to cause the driving means to actuate the air pumping means intermittently at preselected intervals to draw said predetermined volume of air through said air filter;
counting means within the housing, associated with said driving means and adapted to count and record the number of actuations of the air pumping means during a given time period;
a power supply means electrically powering the driving means, timer and counting means;
a clothing attachment means mounted on the outside of the housing and a pocket switch associated with the clothing attachment means and electrically connected to the power supply means, said pocket switch adapted to be electrically closed when the clothing attachment means is operated to attach the sampler to a user's clothing, and electrically open to cut off power from the power supply means when the clothing attachment means is inoperative.

* * * * *